United States Patent [19]

Kato et al.

[11] Patent Number: 5,484,955
[45] Date of Patent: Jan. 16, 1996

[54] TRI-HIGHER ALKYL TIN AZIDE AND ITS USE

[75] Inventors: Takeshi Kato, Higashiosaka; Yasushi Shida, Sakai, both of Japan

[73] Assignee: Takeda Chemical Industries, Ltd., Osaka, Japan

[21] Appl. No.: 83,697

[22] Filed: Jun. 29, 1993

[30] Foreign Application Priority Data

Jul. 6, 1992 [JP] Japan ................................. 4-178484

[51] Int. Cl.$^6$ ............................................. C07D 257/04
[52] U.S. Cl. ................................................................ 552/4
[58] Field of Search ...................................... 552/4

[56] References Cited

U.S. PATENT DOCUMENTS 3,232,958  2/1966  Washington .

FOREIGN PATENT DOCUMENTS 0291969  11/1987  European Pat. Off. .
0253310  1/1988  European Pat. Off. .
9202508  2/1992  WIPO .

OTHER PUBLICATIONS

J. Med. Chem., vol. 34, pp. 2525–2547, (1991).
J. V. Duncia et al., J. Org. Chem., vol. 56, pp. 2396–2400, (1991), entitled "Three Synthetic Routes to a Sterically Hindred Tetrazole. A New One–Step Mild Conversion of an Amide . . . ".

*Primary Examiner*—Rebecca Cook
*Attorney, Agent, or Firm*—Foley & Lardner

[57] ABSTRACT

Disclosed are a compound of the formula $(R)_3SnN_3$, wherein R is a $C_{7-18}$ alkyl, and a process for producing a tetrazolylbenzene compound which comprises reacting a cyanobenzene compound with a $(R)_3SnN_3$. This process is useful for a safe and commercially profitable production of the tetrazolylbenzene compound which is employed for producing a tetrazole derivative having a hypotensive action based on angiotensin II-antagonizing activity or a production intermediate thereof.

1 Claim, No Drawings

1

TRI-HIGHER ALKYL TIN AZIDE AND ITS USE

FIELD OF THE INVENTION

The present invention relates to a novel tri-higher alkyltin azide.

Further, the present invention relates to a commercially valuable and safe process for producing tetrazolylbenzene compounds from cyanobenzene compounds using a tri-higher alkyltin azide. More particularly, the invention relates to a safe and commercially valuable process for producing a tetrazole derivative having a hypotensive action based on angiotensin II-antagonizing activity or a production intermediate thereof.

BACKGROUND OF THE INVENTION

The official gazette of Japanese Patent Laid-open Publication No. 1-117876/1989 discloses the process schematically illustrated below for the production of a tetrazole intermediate for antihypertensive compounds.

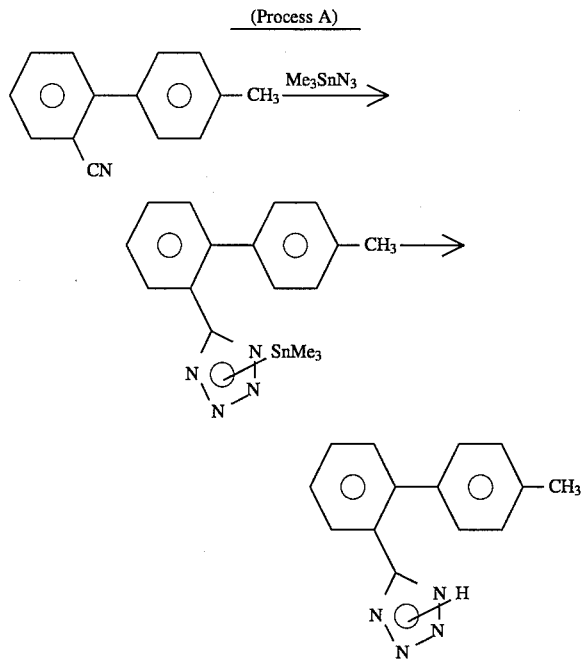

This process comprises reacting the nitrile compound with an excess of trimethyltin azide, separating the crystalline trimethyltin tetrazole derivative from the residual trimethyltin azide by filtration and removing the trimethyltin group with hydrogen chloride to provide the desired tetrazole compound.

Japanese Patent Laid-open Publication No. 63-23868/1988 discloses the following process.

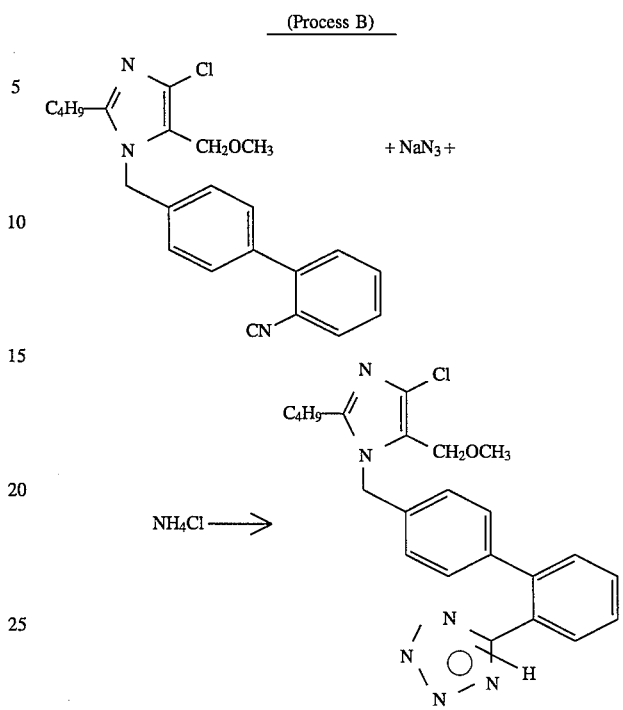

However, Process A described above is disadvantageous, as a commercial production process, in that the overall yield is only 78% and the process involves two reaction steps. Moreover, it is likely that some of the excess trimethyltin azide contaminates the trimethyltin tetrazole derivative produced. It is also likely that when the trimethyltin tetrazole derivative is hydrolyzed with hydrogen chloride, the contaminant trimethyltin azide is decomposed to give rise to the toxic and highly explosive hydrogen azide. Therefore, this process as a commercial process presents a serious safety problem.

On the other hand, in Process B, the range of compatible compounds is limited as compared with the organotin azide process. For example, in the case of a compound in which the substituent in the 2-position of the imidazole ring is a lower alkoxy group, there occurs a decomposition reaction to detract from the product yield. Moreover, since a sublimation of the explosive ammonium azide [N. Irving Sax, Richard J. Lewis, Sr., Dangerous Properties of Industrial Materials, Van Nostrand Reinhold (1989)] occurs during the reaction to cause deposition of the sublimed azide on the condenser or reactor ceiling, the process is less suitable for commercial exploitation from safety points of view.

In either process, it is common practice to use the azide compound in excess for improved yield and reduced reaction time but when the reaction mixture is acidified, the toxic and highly explosive hydrogen azide is released from the unreacted azide compound present in the reaction system.

Since this hydrogen azide is a volatile liquid (boiling point: 37° C.), it is obvious that the worker handling it is exposed to a constant risk. It is reported that hydrogen azide administered in a dose of 0.05 to 0.1 mg/kg induces prostration in man. Moreover, while hydrogen azide as such is a highly explosive substance, it is known that the presence of this substance even in solution at a concentration over 17% is a dangerous cause of explosion, suggesting that an organic composition or system containing this substance at a substantial level is also a major source of hazard. It is also known that hydrogen azide forms explosive salts with heavy metals.

Particularly when an organotin azide such as a trialkyltin azide or triphenyltin azide is employed, the step of hydrolyzing the trialkyltin or triphenyltin tetrazole derivative with an inorganic acid to provide the tetrazole derivative requires a provision for stripping off the hydrogen azide originating from the excess organotin azide from the reaction system and trapping it with an alkaline solution, but since the procedure involved is complicated and very dangerous, the method cannot be utilized commercially.

Also, WO92/02508 discloses the following process.

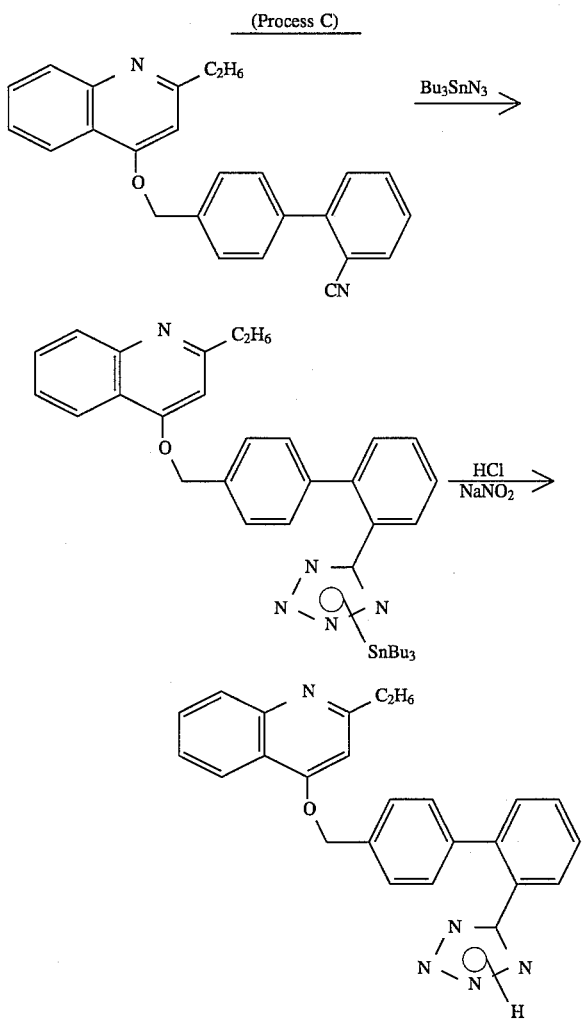

This process comprises reacting the nitrile compound with tributyltin azide and removing the tributyltin group without isolation of the tributyltin tetrazole derivative by addition of aqueous mineral acid to the reaction mixture.

However, tributyltin azide is high in vapor pressure (b.p. 118°–120° C./0.18 mmHg) and has a powerful odor. This odor is an extraordinarily peculiar one, which is readily absorbed by other materials, for example, clothes of workers, reaction vessels or drying machines, and, which, once absorbed, is hard to remove. Besides, tributyltin azide causes, once touching on the skin directly, flush area on the skin, giving rise to rash symptoms such as itching or blisters.

Further, it is known that lower alkyl tin compounds are generally highly toxic [N. Irving Sax, Dengerous Properties of Industrial Materials (1989)]. While tributyltin azide is usually synthesized from tributyltin chloride and sodium azide, the starting tributyltin chloride has also a powerful odor and causes rashes, and its toxicity is so strong as to produce an $LD_{50}$ 129 mg/kg (rats, p.o. Albright and Wilson Ltd., Technical Service Note, "Tributyltin Chloride—Safety and Environmental Protection," March, 1977). Further, tributyltin chloride is absorbed also from the skin.

The workers using tributyltin azide are exposed to a constant risk of hazard such as its peculiar odor absorbed into their clothes, troublesome processes of washing the machines and tools, appearance of rash, odor of the starting material, toxicity and danger of its absorbance from the skin. Therefore, it is difficult to use tributyltin azide on an industrial scale, from the viewpoint that the safety of the workers is not ensured.

SUMMARY OF THE INVENTION

An object of the present invention is to provide a novel tri-higher alkyltin azide, which is represented by the formula (Q) or $(R)_3SnN_3$, wherein R is a $C_{7-18}$ alkyl.

Another object of the present invention is to provide a process for producing a tetrazolylbenzene compound which comprises reacting a cyanobenzene compound with a compound of the formula (Q).

DETAILED EXPLANATION OF THE INVENTION

The inventors of the present invention found unexpectedly after much research how to resolve the problems and to develop a commercial-scale production process for the belowmentioned compound (I) that the desired tetrazole derivative can be produced in one step with safety on a commercial scale by subjecting a suitably substituted cyanobenzene compound (II) and an excess of the compound of the formula (Q) to a 1,3-dipolar cycloaddition reaction to give a trialkyltin tetrazole derivative, adding an aqueous solution of sodium nitrite and a lower alcohol to the reaction mixture containing said derivative and acidifying the mixture with hydrochloric acid whereby the hydrogen azide derived from residual azide compound is safely decomposed without being released from the reaction system and said trialkyltin tetrazole derivative is hydrolyzed without prior isolation from the reaction system.

Thus, when 1.5 to 3 equivalents, relative to the excess trialkyltin azide, of sodium nitrite is added to the reaction mixture prior to hydrolysis and, then, the mixture is rendered acidic for hydrolysis, the released hydrogen azide instantly reacts with nitrous acid quantitatively and decomposes into dinitrogen oxide, nitrogen and water. Since hydrogen azide assumes a bloody red color on admixture with an aqueous solution containing an excess of ferric salt, this color reaction is generally used for its detection. However, this color reaction does not take place in a solution containing nitrous acid, that is to say the reaction mixture in which hydrogen azide has been completely decomposed. Thus, for the production of a tetrazole derivative using a trialkyltin azide on a commercial scale, a method for hydrolyzing such excess organotin azide with safety has been eagerly awaited.

The present invention provides a novel trialkyltin azide of the formula (Q) useful as the agent for forming a tetrazole ring. In the formula (Q), the alkyl R includes straight-chain and branched $C_{7-18}$ alkyl groups, for example, heptyl, octyl, nonyl, decyl, undecyl, dodecyl, tridecyl, tetradecyl, pentadecyl, hexadecyl, heptadecyl, octadecyl, nonadecyl, eicosyl and so on, with preference given to straight-chain $C_{7-18}$ alkyl groups. Among them, alkyl groups of not more than 10 carbon atoms are the more preferred, with the most preference given to n-octyl. Trioctyltin azide in which R represents n-octyl is sparingly toxic and substantially odorless. Moreover, trioctyltin azide in which R represents n-octyl can be used most advantageously, for it can be easily recovered from the reaction mixture.

The compound of the formula (Q) is produced by the method stated below:

In accordance with the method described on p.881 of Organic Synthesis, Coll. Vol. IV 1963, tetraalkyltin chloride is synthesized from alkyl halide, then, trialkyltin chloride is synthesized in accordance with the method disclosed by G. J. M. Van Der Kerk and J. G. A. Luijten, on Journal of Applied Chemistry, 6. 93(1956). Further, by the method disclosed by J. G. A. Luijten et al. on Recueil des Travaux Chimiques des Pays-Bas, 81, 202(1962), 81, 202(1962), tri-higher alkyltin azide can be synthesized.

The above reaction of trialkyltin chloride with sodium azide is carried out in a solvent or no solvent. The solvent is not limited in kind, provided that it does not interfere with the reaction, although diethyl ether, toluene, water etc. are preferred, that is, sodium azide can react in a suspension or in a solution. The amount of the solvent is not critical but is preferably 0.2 times to 10 times the amount of the starting material. The amount of sodium azide is not critical but it is economically advisable to use 1 to 3 equivalents based on the trialkyltin chloride. The reaction temperature is not critical but is generally 2° C.–130° C. and preferably 5° C.–120° C. The reaction time is not limited, either, but is preferably 1 to 10 hours for most practical purposes.

As the compound of the formula (Q) has a low vapor pressure and less odor, it is easy to handle, and, besides, it does not cause rashes to workers, thus being safe for them. The yield of tetrazolation is substantially the same as or even higher than that of a tri-lower alkyltin azide. While azides are generally known as explosive substances, a tri-higher alkyltin azide is considered to be less explosive than a tri-lower alkyltin azide. This is supported also by the fact that, for example, trioctyltin azide is decomposed exothermally at 303° C. while tributyltin azide is decomposed exothermally at 295° C. when measured by means of Differential Scanning Calorimeter.

And, acute toxicities of tributyltin azide were compared with those of trioctyltin azide by oral administration to rats, resulting in that, while the $LD_{50}$ of tributyltin azide was 400 mg/kg in male animals and 200–400 mg/kg in female animals, that of trioctyltin azide was higher, i.e. 500–1000 mg/kg in male and 250–500 mg/kg in female. In both groups receiving trioctyltin azide (500 mg/kg or more) and tributyltin azide (100 mg/kg or more), critical signs such as decreased activity, hyporectivity and abnormal position were observed. In addition to these findings, the rats receiving tributyltin azide (100 mg/kg or more) exhibited salivation (immediately after administration) and severe diarrhea (2–4 days), which suggested direct local irritation by this compound of the gastrointestinal tracts. At necropsy, the rats receiving tributyltin azide exhibited diarrhea and showed fluid in the intestinal tracts, whereas in the rats receiving trioctyltin azide no abnormalities attributed to the test compound were observed except for congestion or hypermia of the lung. Therefore, trioctyltin azide was somewhat less toxic with respect to the mortality and LD50 value. Judging from clinical signs and necropsy finding, tributyltin azide was more toxic than trioctyltin azide.

The starting material of trioctyltin azide, one of the tri-higher alkyltin azides, is trioctyltin chloride, and the $LD_{50}$ of trioctyltin chloride is 4000 mg or higher (rats, p.o.

A. Bokranz and H. Plum, "Industrial Manufacture and Use of Organotin Compounds," Schering AG, Bergkamen, W. Germany, March, 1975). Therefore, trioctyltin chloride can be used safely even in the case of producing trioctyltin azide. Therefore, a tri-higher alkyltin azide is remarkably excellent as a tetrazolating agent.

Further, the present invention provides a process for producing a tetrazolylbenzene compound characterized by reacting a cyanobenzene compound with the compound of the formula (Q) and more particularly to a process for producing a compound of the formula (I) which comprises reacting a compound of the formula (II) with a compound of the formula (Q) and then acidifying the reaction mixture in the presence of nitrous acid or a salt thereof.

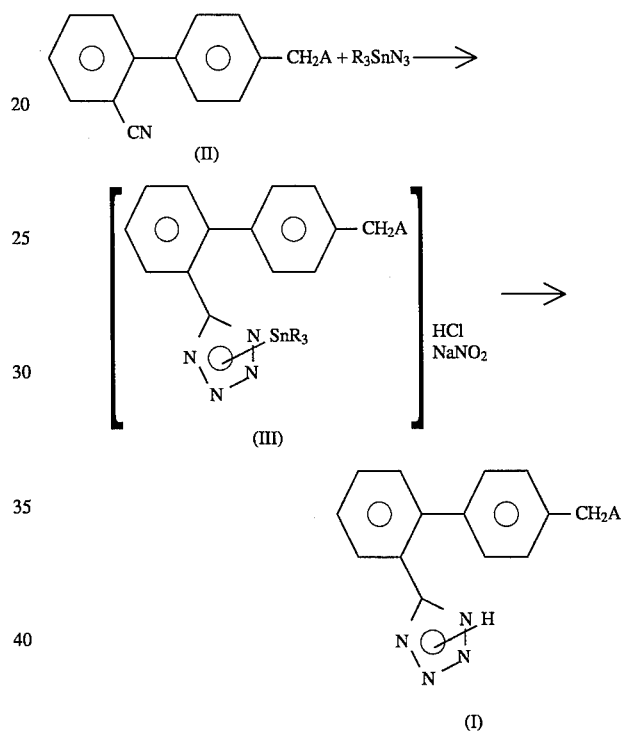

wherein A represents hydrogen, a phthalimido or a group of the formula

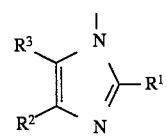

wherein $R^1$ represents an alkyl group which may be substituted and bound to the imidazole ring through a hetero atom; $R^2$ and $R^3$ each represents hydrogen, halogen, formyl, alkoxycarbonyl or alkyl which may be substituted by hydroxy or $R^2$ and $R^3$ may jointly form a benzene ring in combination with the two adjacent carbon atoms on the imidazole ring.

The cyanobenzene compound is not specifically limited, provided that it is a compound having a cyano group on a benzene ring and being capable of reacting with a trialkyltin azide of the formula (Q) to form a tetrazole ring. Among such compounds, compounds of the above formula (II) are preferred.

Referring to the formula (I), $R^1$ is an alkyl or other group which may be substituted and be bound through a hetero atom (e.g. —O—, —S—, —NH—), thus including lower $(C_{1-4})$alkyl, lower $(C_{1-4})$alkoxy, lower $(C_{1-4})$ alkylthio and lower $(C_{1-4})$alkylamino. Particularly preferred are ethoxy and butyl.

$R^2$ and $R^3$ include hydrogen, halogen (e.g. Cl, Br, I), formyl, alkoxycarbonyl (e.g. lower $(C_{1-4})$alkoxycarbonyl), alkyl which may be substituted by hydroxy (e.g. lower $(C_{1-4})$alkyl, hydroxymethyl), and so on.

Referring to the formula (II), where $R^2$ and $R^3$ form a benzene ring, substituent groups (preferably numbering 1 or 2) on the benzene ring include lower $(C_{1-4})$alkyl, halogen, lower $(C_{1-4})$alkoxy, lower $(C_{1-4})$alkoxycarbonyl, phenyl-lower $(C_{1-4})$alkoxycarbonyl and so on. The preferred examples of A in formula (II) are groups of the formula

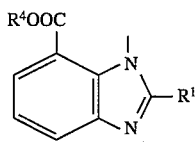

wherein $R^1$ is as defined hereinbefore; $R^4$ represents hydrogen or lower $(C_{1-4})$alkyl (preferably methyl, ethyl) which is optionally substituted with hydroxyl, amino, halogen, a lower $(C_{2-6})$ alkanoyloxy (e.g. acetyloxy, pivaloyloxy, etc.), 1-lower $(C_{1-6})$ alkoxycarbonyloxy (e.g. methoxycarbonyloxy, ethoxycarbonyloxy, cyclohexyloxycarbonyloxy, etc.) or a lower $(C_{1-4})$ alkoxy. The more preferred are groups of the formula

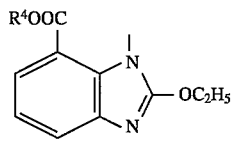

wherein $R^4$ is as defined above.

The trialkyltin azide of the formula (Q) is capable of reacting with a cyanobenzene compound to form a tetrazole ring.

In the process of the present invention, the alkyl R of the formula (Q) includes straight-chain and branched $C_{7-18}$ alkyl groups, for example, heptyl, octyl, nonyl, decyl, undecyl, dodecyl, tridecyl, tetradecyl, pentadecyl, hexadecyl, heptadecyl, octadecyl, nonadecyl, eicosyl and so on, with preference given to straight-chain $C_{7-18}$ alkyl groups. Among them, alkyl groups of not more than 10 carbon atoms are the more preferred, with the most preference given to n-octyl. Trioctyltin azide in which R represents n-octyl is sparingly toxic and substantially odorless. Moreover, trioctyltin azide in which R represents n-octyl can be used most advantageously, for it can be easily recovered from the reaction mixture.

Referring to nitrous acid or a salt thereof, a salt of nitrous acid with an alkali metal, such as sodium or potassium, is preferred and, in particular, sodium nitrite is advantageous. In acidifying the reaction mixture in the presence of nitrous acid or a salt thereof, the reaction mixture is preferably adjusted with an inorganic acid to pH ≦ about 4 and, for still better results, to pH about 1 to 3. The inorganic acid mentioned above includes hydrochloric acid, sulfuric acid, phosphoric acid, etc., although hydrochloric acid is particularly preferred.

The above reaction is carried out in a solvent. The solvent is not limited in kind, provided that it does not interfere with the reaction, although comparatively high-boiling organic solvents such as toluene, xylene, dimethylformamide, dimethylimidazolidinone, etc. are preferred. The amount of the solvent is not critical but is preferably 3 to 10 times the amount of the starting material. The reaction temperature is generally 90° C. to 150° C. and preferably 100° C. to 130° C. The amount of trialkyltin azide of the formula (Q) is not critical but it is economically advisable to use 1 to 3 equivalents based on the cyanobenzene compound. The reaction time is not limited, either, but is preferably 5 to 40 hours for most practical purposes. Moreover, the reaction is carried out in a one pot reaction, that is, a mixture of the cyanobenzene, trialkyltin chloride, sodium azide and the solvent is stirred under the conditions above mentioned and treated to give the desired tetrazole derivative.

The conditions, under which the hydrogen azide formed on acidolysis of the trialkyltin azide is decomposed by nitrous acid or a salt thereof, are not critical but the temperature is preferably maintained between 5° C. and 40° C. Any residue of nitrous acid at the end of this treatment indicates that the decomposition reaction has been successfully completed. Theoretically the amount of nitrous acid or a salt thereof need not be over one equivalent relative to the excess azide compound but it is safe and economical to use 1.2 to 3 equivalents.

Because the excess azide can thus be safely decomposed by acidifying the reaction mixture in the presence of nitrous acid or a salt thereof, the trialkyltin tetrazole derivative need not be separated from the reaction mixture and, moreover, can be easily hydrolyzed to provide the tetrazolylbenzene compound. Furthermore, the desired compound can be caused to separate out as crystals in many cases. Isolation and purification of the tetrazolylbenzene compound can be effected by the routine procedure (e.g. filtration, extraction, concentration, recrystallization, column chromatography, etc.). Particularly with trioctyltin azide, the liposolubility of which is higher than that of a tri-lower alkyl tin compound, it is likely that removal of the organic tin compound residue from the product compound will be facilitated.

In accordance with the present invention, tetrazolylbenzene compounds, particularly tetrazole derivatives having a hypotensive action based on angiotensin II—antagonizing activity, or production intermediates thereof, can be obtained safely and in good yield. The invention is, therefore, of value as a commercial process for producing tetrazolylbenzene compounds.

The working examples and the reference examples are intended to describe the invention in further detail and should by no means be construed as defining the scope of the invention.

EXAMPLE 1

Trioctyltin azide (Tri-n-octyltin azide)

In 30 ml of pure water was dissolved 10.19 g of sodium azide and the solution was cooled to 8° C. Then, 50.0 g of trioctyltin chloride was added dropwise over a period of 10 minutes and the mixture was stirred at the same temperature for 2 hours. The reaction mixture was then extracted with 88 ml of methylene chloride and further with 25 ml of the same solvent, and the extract was washed with 25 ml of 10% aqueous sodium chloride solution and concentrated to provide 50.05 g of trioctyltin azide.

IR(film): 2924, 2856, 2080, 1466cm$^{-1}$.

EXAMPLE 2

Tridodecyltin azide (Tri-n-dodecyltin azide)

To 3.18 g of magnesium was added 10 ml of the solution prepared by dissolving 30 g of dodecyl chloride in 60 ml of diethyl ether. To the mixture was added two drops of bromine. The mixture was stirred for a while. When reflux was started, the remaining solution was added dropwise to the reaction mixture. After completion of the exothermic reaction, the reaction mixture was heated and stirred for 30 minutes under reflux. The reaction mixture was cooled with ice, to which was added 5.29 g of stannic chloride. The mixture was stirred for one hour under reflux. Diethyl ether was distilled off, and the residue was stirred for 1.5 hour at 65° C. The reaction mixture was cooled and there were added diethyl ether and 10% hydrochloric acid. The mixture was shaken and was then left standing to form two layers. The organic layer was separated and dried over calcium chloride, and then concentrated under reduced pressure. To the concentrate was added 1.76 g of stannic chloride. The mixture was stirred for 3 hours at 200° C., once cooled and then stirred for further 3 hours at 200° C. The reaction mixture was cooled and then there was added methylene chloride. Insolubles were filtered off, and the filtrate was washed with water, then dried over magnesium sulfate, followed by concentration under reduced pressure. The concentrate was added dropwise to a solution of 3.44 g of sodium azide in 10 ml of water at 4° C., followed by stirring for 1.5 hour. The reaction mixture was subjected to extraction with methylene chloride. The extract was dried over magnesium sulfate, and then concentrated to afford 21.59 g of tridodecyltin azide.

IR(film): 2928, 2856, 2080, 1468 cm$^{-1}$

EXAMPLE 3

Trioctadecyltin azide (Tri-n-octadecyltin azide)

A mixture of 20.0 g of trioctadecyltin chloride, 3.0 g of sodium azide and 40 ml of toluene was stirred at 120° C. for 6 hours. After cooling, 100 ml of toluene was added to the reaction mixture. The toluene layer was washed with water, dried over magnesium sulfate and concentrated under reduced pressure to give 13.8 g of trioctadecyltin azide.

IR(film): 2128, 2056 cm$^{-1}$.

EXAMPLE 4

5-[2-(4'-methylbiphenyl)]-1H-tetrazole

A mixture of 4.85 g of 2-(4-methylphenyl)benzonitrile, 37.46 g of trioctyltin azide (tri-n-octyltin azide) and 24 ml of toluene was stirred at 125° C. for 8.5 hours. After cooling, the reaction mixture was concentrated. To the residue was added 43 ml of ethanol as well as an aqueous solution of sodium nitrite (5.4 g/21 ml) and the mixture was adjusted to pH 3 with hydrochloric acid. Then, 10 ml of ethyl acetate and 30 ml of n-hexane were added and the mixture was adjusted to pH 1 with concentrated hydrochloric acid. After confirmation of precipitation, the mixture was adjusted to pH 3 with 30% aqueous sodium hydroxide solution and the crystals were separated. At this junction, ferric chloride TS was added to a sample of the liquid phase but no red color developed. On drying, 4.45 g of crystals were obtained. The mother liquor was extracted with methylene chloride and the methylene chloride layer was washed with water and extracted with 1N aqueous sodium hydroxide solution. The sodium hydroxide layer was washed with methylene chloride and adjusted to pH 2.6 with concentrated hydrochloric acid and the resulting crystals were separated. On drying, 1.56 g of crystals were obtained. The crops of crystals were combined and dissolved in 25 ml of ethyl acetate under heating and after 25 ml of n-hexane was added the solution was cooled. The resulting crystals were separated and washed with 25 ml of ethyl acetate/n-hexane mixture (1:1). On drying, 5.14 g of 5-[2-(4'-methylbiphenyl)]- 1H-tetrazole was obtained. Yield 87%. $^1$H NMR (CDCl$_3$) δ: 2.40 (3H, s), 7.16 (4H, dd), 7.40 (t)[1], 7.43 (d)[1], 7.55 (2H, quintet-d), 8.15 (d)[2], 8.19 (t)[2]

Note: 1) 7.40 & 7.43 1H; 2) 8.15 & 8.19 1H IR(KBr): 1604, 1570, 1486, 1452, 1400, 1248, 1162, 1080, 1052, 1010, 912, 826, 776, 756, 556, 522, 450 cm$^{-1}$.

EXAMPLE 5

Methyl 2-ethoxy-1-[2'-(1H-tetrazol-5-yl)biphenyl-4-yl]methylbenzimidazole-7-carboxylate A mixture of 13.0 g of methyl 1-(2'-cyanobiphenyl-4-yl)methyl-2-ethoxybenzimidazole-7-carboxylate, 47.1 g of trioctyltin azide (tri-n-octyltin azide) and 60 ml of toluene was refluxed at 125° C. for 31 hours. After cooling, the reaction mixture was concentrated. To the concentrate was added 56 ml of ethanol as well as an aqueous solution of sodium nitrite (7.7 g/28 ml) and the mixture was adjusted to pH 5 with concentrated hydrochloric acid. Then, 31 ml of ethyl acetate was added. The mixture was further adjusted to pH 1.1 with concentrated hydrochloric acid, diluted with 20 ml of n-hexane and adjusted to pH 3.3 with 1N aqueous sodium hydroxide solution. The crystals were separated, washed with ethyl acetate/n-hexane mixture (1:3) and dried to provide 14.56 g of methyl 2-ethoxy-1-[2'-(1H-tetrazol-5-yl)biphenyl-4-yl]methylbenzimidazole-7carboxylate.

Yield 100%. $^1$H NMR (CDCl$_3$) δ: 1.42 (3H, t), 3.56 (3H, s), 4.27 (2H, q), 5.54 (2H, s), 6.70 (2H, d), 6.78–6.95 (4H, m), 7.28–7.33 (1H, m), 7.40 (1H, dd), 7.56–7.66 (2H, m), 8.02–8.06 (1H, m)

IR(KBr): 1720, 1618, 1548, 1476, 1432, 1390, 1354, 1324, 1284, 1222, 1134, 1042, 872, 840, 820, 780, 756 cm$^{-1}$.

EXAMPLE 6

5-[2-(4'-phthalimidomethylbiphenylyl)]-1H-tetrazole

A mixture of 3.00 g of 4-(2-benzonitrile)-benzylphthalimide, 13.3 g of trioctyltin azide (tri-n-octyltin azide) and 15 ml of toluene was stirred at 115°–120° C. for 29 hours. After cooling, the reaction mixture was concentrated. To the residue was added 16 ml of ethanol as well as an aqueous solution of sodium nitrite (2.0 g/8 ml) and the mixture was adjusted to pH 3.1 with concentrated hydrochloric acid. Then, 5 ml of ethyl acetate and 15 ml of n-hexane were added and the mixture was cooled. The crystals formed were separated, washed with 30 ml of n-hexane and dried to provide 3.51 g of 5-[2-(4'-phthalimidomethylbiphenylyl)]-1H-tetrazole. Yield 100%. $^1$H NMR (CDCl$_3$) δ: 4.78 (2H, s), 7.9–8.0 (12H, m) IR(KBr): 1770, 1714, 1466, 1436, 1396, 1346, 1090, 944, 768, 758, 718, 630, 530 cm$^{-1}$

EXAMPLE 7

2-Butyl-4-chloro-5-formyl-1-[2'-(1H-tetrazol-5-yl)biphenyl- 4-yl]methylimidazole A mixture of 2.11 g of 2-butyl-4-chloro-5-formyl- 1-(2'-cyanobiphenyl-4-yl)methylimidazole, 8.38 g of trioctyltin azide (tri-n-octyltin azide) and 10 ml of toluene was stirred at 120° C. for 18 hours. After cooling, the reaction mixture was concentrated. To the residue was added 10 ml of ethanol as well as an aqueous solution of sodium nitrite (1.3 g/5 ml) and the mixture was adjusted to pH 3.3 with concentrated hydrochloric acid. The mixture was diluted with 20 ml of water and extracted with two 20 ml portions of ethyl acetate. The ethyl acetate solution was concentrated and the residue was purified by chromatography on 30 g of silica gel ($CH_2Cl_2$-MeOH). The active fraction was concentrated to provide 1.82 g of 2-butyl-4-chloro-5-formyl- 1-[2'-(1H-tetrazol-5-yl)biphenyl-4-yl] methylimidazole. Yield 73%. $^1$H NMR ($CDCl_3$) δ: 0.78–1.80 (9H), 2.53 (3H, t), 5.51 (2H, s), 6.9–8.0 (12H, m), 9.66 (1H, s) IR(KBr): 2964, 1668, 1518, 1466, 1382, 1280, 758 $cm^{-1}$

EXAMPLE 8

2-Butyl-4-chloro-5-(hydroxymethyl)-1-[[2'-(1H-tetrazol-5-yl)biphenyl-4-yl]methylimidazole A mixture of 5 g of 2-butyl-4-chloro-1-[(2'-cyanobiphenyl- 4-yl)methyl]-5-(hydroxymethyl)imidazole, 30.2 g of trioctyltin azide (tri-n-octyltin azide), 25 ml of toluene and 1 ml of dimethylformamide was stirred for 24 hours at 115° C. in nitrogen streams. The reaction mixture was, after cooling, concentrated, and there were added 40 ml of ethanol and a solution of 5.2 g of sodium nitrite in 19 ml of water, whose pH was adjusted at 3.4 with conc. hydrochloric acid. The resultant mixture was subjected to extraction with methylene chloride, and the extract was concentrated under reduced pressure. To the concentrate was added hexane, then resulting crystalline precipitates were collected by filtration. The crystals were washed with hexane, then dried to afford 5.27 g (yield 94.7%) of 2-butyl- 4-chloro-5-(hydroxymethyl)-1-[[2'-(1H-tetrazol-5-yl)biphenyl- 4-yl]methyl]imidazole. The NMR spectrum of the product was in good agreement with that described in J. Med. Chem., 1991, 34, 2525.

EXAMPLE 9

5-[2-(4'-methylbiphenyl)]-1H-tetrazole

A mixture of 1.50 g of 2-(4-methylphenyl)benzonitrile, 19.5 g of tridodecyltin azide (tri-n-dodecyltin azide) and 7 ml of toluene was stirred for 37.5 hours at 120° C. The reaction mixture was, after cooling, concentrated, and there were added 18 ml of ethanol, 1 ml of methylene chloride and 2.4 g of sodium nitrite dissolved in 9 ml of water, whose pH was adjusted at 3.4 with conc. hydrochloric acid. To the mixture were added 2 ml of ethyl acetate and 100 ml of hexane. Insolubles were filtered off. The filtrate was shaken, then left standing to form two layers. The organic layer was subjected to extraction with 1N NaOH. The alkaline layer was adjusted at pH 3 with conc. hydrochloric acid, and then subjected to extraction with ethyl acetate. The extract was concentrated, and there were added ethyl acetate and hexane to cause crystallization. The crystals were collected by filtration, washed with hexane and dried to afford 1.51 g (yield 82.3%) of 5-[2-(4'-methylbiphenyl)]tetrazole. Spectrum data were in good agreement with those in Example 4.

EXAMPLE 10

5-[2-(4'-Methylbiphenyl)]-1H-tetrazole

A mixture of 0.50 g of 2-(4-methylphenyl)benzonitrile and 13.6 g of trioctadecyltin azide (tri-n-octadecyltin azide) was stirred for 13.5 hours at 120° C. The reaction mixture was processed in substantially the same manner as in Example 9 to afford 0.499 g (yield 81.6% ) of 5-[2-(4-methylbiphenyl)]-1H-tetrazole. Spectrum data were in good agreement with those in Example 4.

What is claimed is:

1. A compound of the formula $(R)_3SnN_3$, wherein R is n-octyl.

* * * * *